United States Patent [19]

Cortes et al.

[11] Patent Number: 4,529,521
[45] Date of Patent: Jul. 16, 1985

[54] METHOD AND APPARATUS FOR ANALYZING LATEXES

[75] Inventors: Hernan J. Cortes, Midland, Mich.; James C. Davis, Hudson, Ohio

[73] Assignee: The Dow Chemical Company, Midland, Mich.

[21] Appl. No.: 526,921

[22] Filed: Aug. 26, 1983

[51] Int. Cl.³ .............................................. B01D 15/08
[52] U.S. Cl. .................................. 210/635; 210/644; 210/656; 210/198.2; 210/321.1; 422/70; 436/161
[58] Field of Search ............... 210/634, 635, 644, 649, 210/656, 198.2, 321.1; 422/70; 436/161

[56] References Cited

U.S. PATENT DOCUMENTS

| 2,049,828 | 8/1936 | Stevens | 210/646 |
| 2,797,149 | 6/1957 | Skeggs | 422/70 |
| 3,028,965 | 4/1962 | Isreeli et al. | 210/149 |
| 3,495,943 | 2/1970 | Kapff | 422/70 |
| 3,915,648 | 10/1975 | Stein | 210/321.1 |
| 4,082,659 | 4/1978 | Heinze et al. | 210/644 |
| 4,123,353 | 10/1978 | Hakansson et al. | 210/321.1 |
| 4,160,726 | 7/1979 | DelPico | 210/433.1 |
| 4,229,542 | 10/1980 | Nylen | 210/321.1 |
| 4,233,030 | 11/1980 | Twitchett et al. | 422/70 |
| 4,301,118 | 11/1981 | Eddleman | 210/321.1 |
| 4,448,691 | 5/1984 | Davis | 210/656 |
| 4,451,369 | 5/1984 | Sekino et al. | 210/321.1 |

OTHER PUBLICATIONS

Automatic Dialyzing-Injection System for Liquid Chromatography of Ions and Small Molecules by Nordmeyer et al., Analytical Chemistry, vol. 54, No. 14, Dec. 1982, pp. 2605–2607.

Application of Diafiltration Technique in Latex Studies by Labib et al., Journal of Colloid and Interface Science, vol. 67, No. 3, Dec. 1978, pp. 543–547.

Cleaning Surface Latexes Characterization by Serium Replacement by Ahmed et al., Journal of Coloid and Interface Science, vol. 73, No. 2, Feb. 1980, pp. 388–405.

Primary Examiner—John Adee
Attorney, Agent, or Firm—Joe R. Prieto

[57] ABSTRACT

A method for analyzing the serum phase of a latex solution by permeating low molecular weight components present in the serum phase for a known amount of time through a size selective permeable membrane to a dialysate fluid and sequentially injecting the dialysate fluid into a liquid chromatograph for subsequent analysis.

9 Claims, 3 Drawing Figures

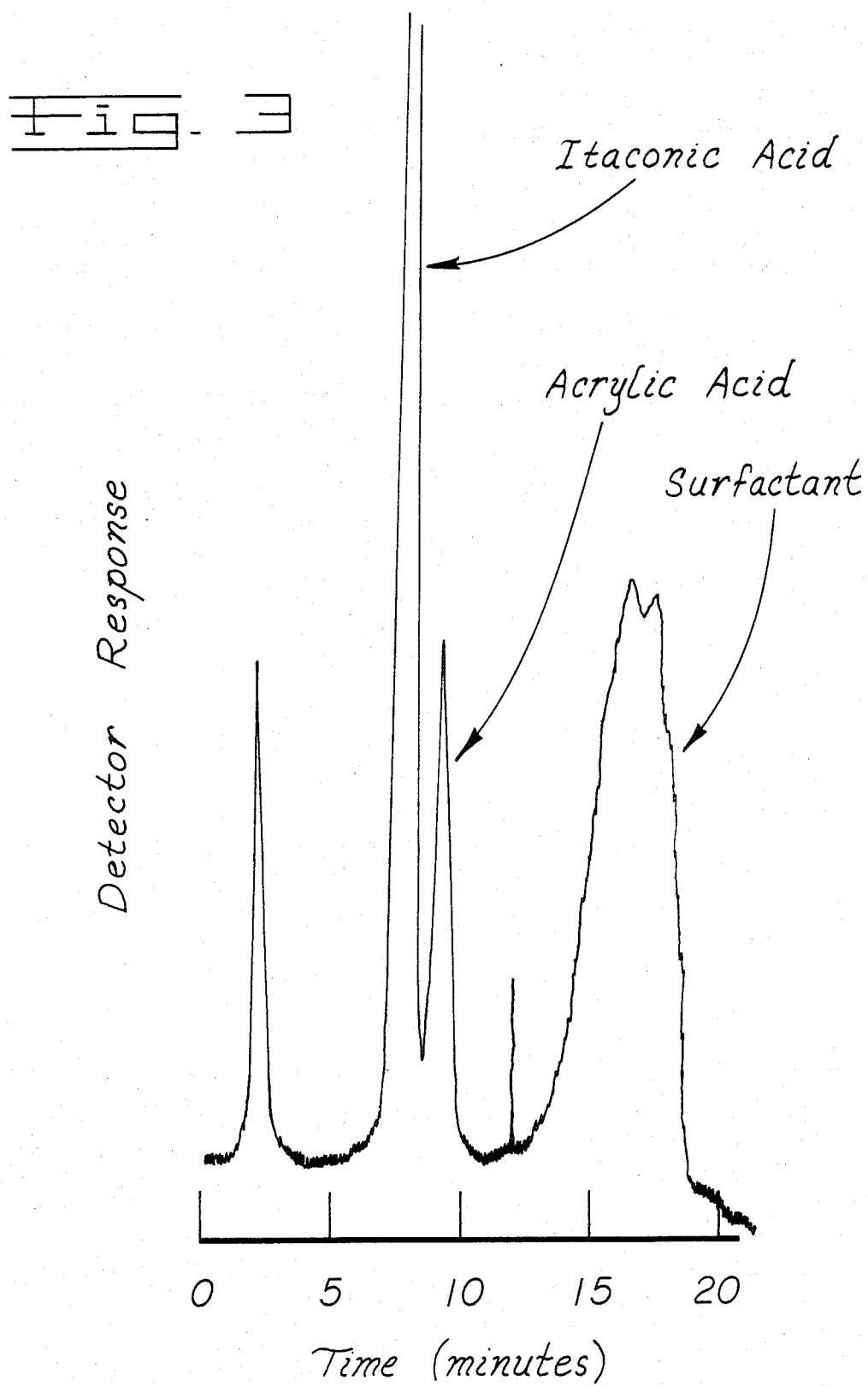

METHOD AND APPARATUS FOR ANALYZING LATEXES

BACKGROUND OF THE INVENTION

This invention relates to a method and apparatus for analyzing a latex solution and more particularly to a method and apparatus for analyzing the serum phase of a latex solution for the presence of low molecular weight components.

Typically, the serum phase of a latex solution may contain low molecular weight components such as surfactants, stabilizers, inorganic salts, and residual monomers which can be difficult to separate from the polymer.

Heretofore, in order to analyze for low molecular weight components present in the serum phase of a latex solution it has been necessary to separate or remove the macromolecular latex particles or dispersion from the serum phase of the latex solution independent from and prior to analysis of a sample of the serum phase. Several methods used to carry out the separation or removal of the latex from the serum phase of the latex suspension include, for example, dialysis, ultrafiltration, ultracentrifugation, precipitation, or coagulation.

Although the above methods are satisfactory for separating the latex serum phase from the latex, the methods above are complex and require a relatively longer period of time to ultimately analyze the components in the serum phase.

It is desired to provide a more rapid and relatively continuous method and apparatus for analyzing the low molecular weight components in the serum phase of a latex solution.

SUMMARY OF THE INVENTION

An improved method of analyzing the serum phase of a latex solution involves contacting one side of a size selective molecularly permeable membrane with the latex solution while contacting the other side of the membrane with a dialysate fluid. Low molecular weight components are allowed to permeate, for a known amount of time, through the membrane to the dialysate fluid side. Thereafter, the dialysate fluid is displaced from contact with the membrane and an aliquot of the displaced dialysate fluid is captured. This captured sample is added to a chromatographic column and eluted with eluent. The sample of dialysate fluid is analyzed for serum phase species of interest.

The apparatus of the invention includes a membrane device having a size selective molecularly permeable membrane in combination with a liquid chromatographic analysis apparatus.

BRIEF DESCRIPTION OF THE DRAWINGS

FIG. 3 is an example of a chromatograph of a latex solution analyzed according to the method of the present invention.

TERMS

A "latex solution" as used in the present invention is any colloidal suspension suitable for membrane permeation. The suspension may have low molecular weight components capable of being permeated through a permeable membrane. A latex solution is intended to include the aqueous suspensions of a hydrocarbon polymer occurring naturally or made synthetically. An example of a natural latex is that of the tropical *Hevea braziliensis* which is a source of rubber. Synthetic latexes include, for example, those made by emulsion polymerization techniques from styrene-butadiene copolymer, acrylate resins, polyvinyl acetate, and similar materials.

The "serum phase" of a latex solution means the liquid phase or aqueous suspension which remains after removing the solid latex colloidal particles dispersed therein. Additives such as surfactants, stabilizers, inorganic salts and residual monomers may be present in the serum phase.

A "membrane device" refers to any device having a size-selective molecularly permeable membrane of any configuration, for example, tubes or flat sheets, and means for contacting the membrane with a latex solution. Preferably the membrane is a hollow fiber membrane. By a "hollow fiber membrane" it is meant a small tube or fiber having an internal diameter of less than one millimeter, preferably from about 80 to about 100 micrometers and being composed of a size-selective molecularly permeable membrane material.

"Size-selective membrane" in this invention refers to any of the various membranes which has the property of being permeable and is further characterized by allowing only substances with a certain molecular weight to permeate therethrough. For example, the membrane may be a cellulose membrane. Membranes having a molecular weight cut off of 5,000 or less are preferably used.

"Dialysate fluid" in this invention means any liquid medium contacting one side of the size selective membrane used for the purpose of collecting any low molecular weight components that may permeate through the membrane. The dialysate fluid is further characterized by being inert to the membrane, the serum phase component permeated through the membrane and the eluent of the chromatographic system. Suitably, the dialysate fluid may be water.

DESCRIPTION OF THE PREFERRED EMBODIMENTS

Figure 1:
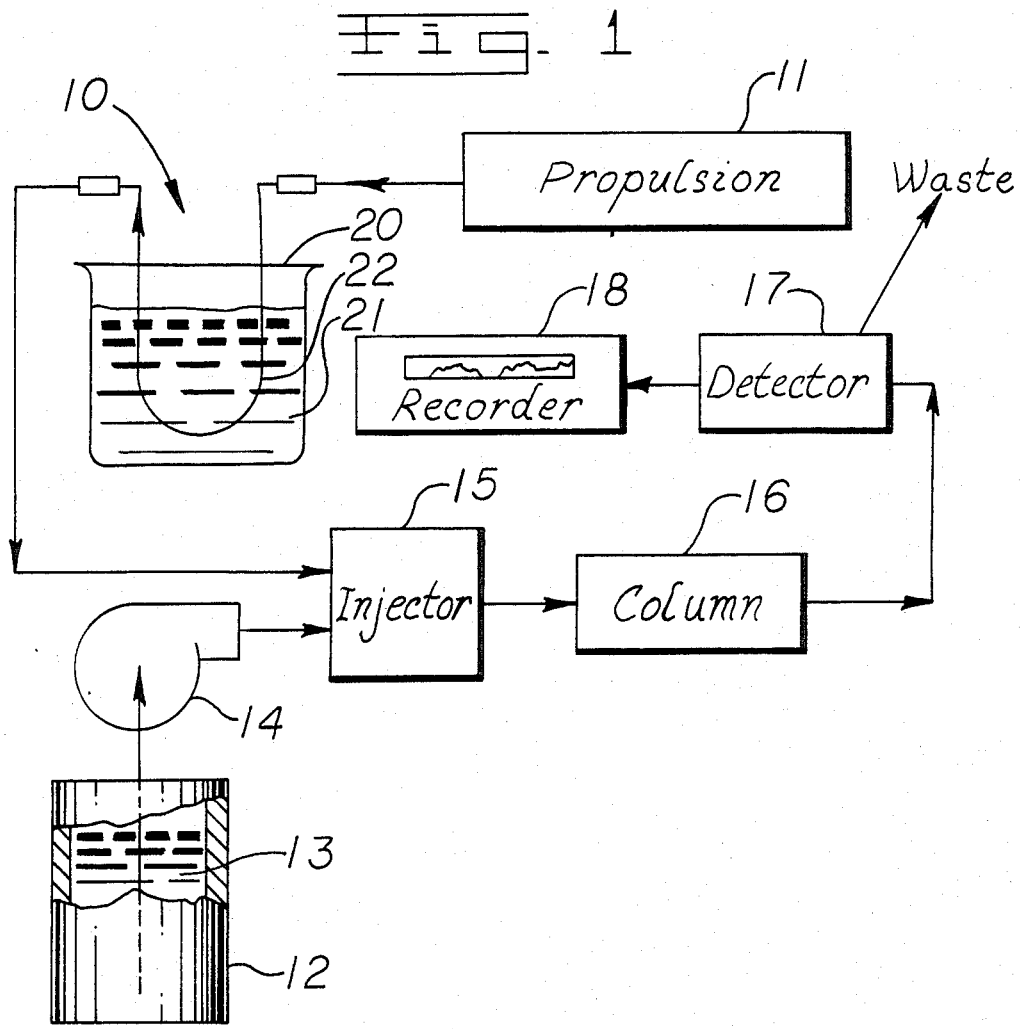
FIG. 1 is a schematic illustration of the apparatus of the present invention.

Referring to FIG. 1, there is shown a membrane device 10 in combination with a liquid chromatographic system. The chromatographic system includes a chromatographic column 16 which comprises a housing containing a separating means in the form of a particulate packing or gel through which a sample solution is eluted to separate into component species. Several types of separating means may be used to construct a suitable chromatographic column as described in *Basic Liquid Chromatography* by Johnson and Stevenson, Varian Associates, Inc., Palo Alto, Calif., 1978. The choice of separating means used is dependent somewhat on the component species desired to be separated. The eluent used is also largely dependent on the component species desired to be analyzed. The eluent, however, can be any common eluent known in the art of liquid chromatography.

The eluent and column packing can readily be selected based on components to be analyzed by one skilled in the art. A preferred means for adding an eluent solution or mobile phase to the chromatographic column 16 comprises an eluent reservoir 12 containing an eluent solution 13. The eluent solution 13 is withdrawn from the reservoir 12 by a pump 14.

A sample injection valve 15 is the preferred means for adding a sample to the chromatographic system. Connected to the sample injection valve 15 is the membrane device 10 which will be described in detail below. A sample is added to the sample injection valve 15 by first displacing sample containing component species of interest from the membrane device 10 using propulsion means 11, preferably a syringe. Sample added to the system at valve 15 is swept through the apparatus by the pumped eluent solution to the chromatographic column 16. The sample is eluted through column 16 and component species thereof ultimately appear chromatographically displaced in the chromatographic column effluent which is delivered to the detector means 17.

In the detector, the effluent produces an electrical signal proportional to the property monitored, such as, for example, light absorbance, fluorescence, and which signal is conducted from the detector to a recorder 18, such as, for example, a strip chart recorder, an integrator and the like, all of which are well known to the art.

Figure 2:
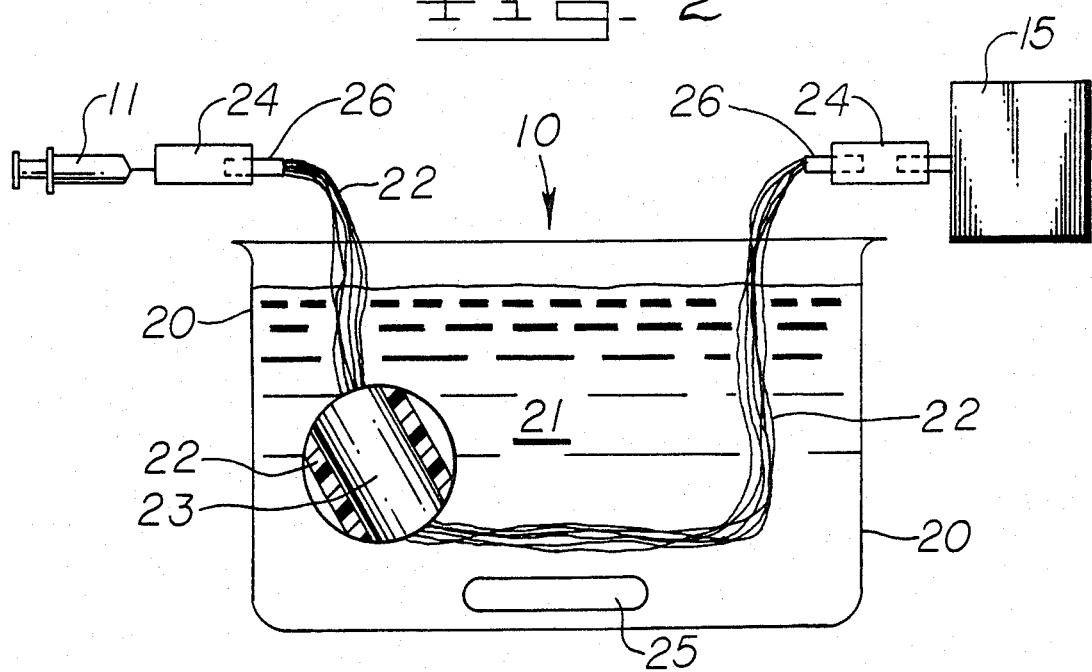
FIG. 2 depicts one of the preferred membrane devices of the present invention connected to an injection valve of a chromatographic column.

With reference to FIG. 2, there is shown a simplified and preferred form of the membrane device which comprises an open-top latex solution reservoir or container 20, preferably made of glass or a similar inert material. Contained in the reservoir 20 is a latex solution 21. The reservoir 20 may optionally contain an agitating means 25 which may be, for example, a magnetic stirring bar 25 for stirring the latex solution 21. A hollow fiber or plurality of fibers 22 are suspended in the latex solution between connection means 24 at each end of the fibers. At least 95 percent of the fibers length should be submerged in the latex solution for greater permeation.

The end of a single hollow fiber or the ends of a plurality of fibers 22 may be held together by potting the fiber ends in a hollow tube 26 larger in diameter than the fibers. The potting is accomplished with a solid forming material such as caulk or an epoxy known to those skilled in the art.

A preferred connection means 24 is a short piece of tygon or rubber tubing to connect one end of the hollow fibers to the sample injection valve 15 and to connect the opposite end of the hollow fibers to propulsion means 11. The propulsion device 11 may be any means which displaces the dialysate from the bore or bores 23 of the hollow fibers such as a pump or a syringe. The propulsion means 11 is preferably a syringe as shown in FIG. 2.

The bore or bores 23 of the hollow fiber membranes contain a dialysate fluid. The submergence of bores 23 containing the dialysate fluid into the latex solution 21 promotes permeation of low molecular weight components contained in the serum phase of the latex solution to the dialysate fluid.

In operation of the membrane device described above, the low molecular weight components are allowed to permeate through the hollow fibers for a known amount of time. Once a known elapsed permeation time is reached, additional dialysate fluid is injected into the bores 23 of the hollow fibers 22 to displace a sample of the dialysate fluid initially contained in the bore of the fibers into sample injection valve 15. An equilibrium rate does not have to be reached during permeation. Sample added to the valve 15 is swept through the apparatus by pumped eluent solution to chromatographic column 16. The column eluent is passed through a detector 17 and the various components in the column eluent are recorded on recorder 18. Thereafter, the eluent is dumped as waste product. The total time necessary to carry out the method of the present invention can be minutes, thus providing a rapid and simple method of analysis. The "standard addition" technique for quantitating the components of interest present in the latex solution is used. Identification of components of interest in the sample is made by matching retention times of known components of interest eluted through the column with components of interest in the sample. Both the quantitation and identification techniques are well known in the art of liquid chromatography.

The invention is further illustrated by the following example.

EXAMPLE 1

A 50 gram sample of copolymer of methyl acrylate and vinylidene chloride latex solution, commercially available from The Dow Chemical Company, was placed in a 50 ml beaker.

One end of a hollow fiber bundle unit was connected to a liquid chromatograph injector loop using about 2 cm of 0.25 inch I.D. tygon tubing and the other end of the hollow fiber bundle unit was connected to a syringe with about 2 cm of 0.25 inch I.D. tygon tubing. The hollow fiber bundle unit which is commercially available from Spectrum Medical Industries Inc. under the trade name of SPECTRAPOR* and part number 132275, contained 22 cellulose fibers having a 250 $\mu$l working volume. This unit is particularly suitable for dialysis of solutes with a molecular weight content range of 5000 or below.

The hollow fiber bundle unit was immersed into the beaker of latex solution. Components in the latex solution were allowed to permeate through the membrane for about 10 minutes. The latex solution was stirred constantly with a magnetic stirrer to aid the diffusion of components in the latex serum phase to the surface of the fibers.

The syringe at the end of the hollow fiber bundle unit was used to force the dialysate in the bore of the hollow fiber into the injector loop connected to a liquid chromatographic column with the valve in the load position. The injector loop was then switched to its inject position to allow eluent to elute the sample through the liquid chromatographic column. The volume of dialysate sample injected into the chromatographic column was 50 $\mu$l. The dialysate was chromatographed using ion exclusion liquid chromatography. The column used was 140 mm long by 9 mm I.D. The column packing was an Aminex 50WX4 resin in a particle size of 20 to 30$\mu$ and in the H+ form. The eluent used was a 0.01 N solution of $H_2SO_4$ at a pH of 2 at a flow rate of 1.0 ml/min. The detector was an LDC 1203 ultraviolet detector run at a wavelength of 214 nm.

The chromatogram obtained in this example is shown in FIG. 3. Identification of the compounds extracted was made by matching retention times to injections of known materials. The presence of surfactants was reinforced by analyzing the dialysates by colorimetry (methylene blue method) a method well known in the art.

What is claimed is:

1. A method of analyzing the serum phase of a latex solution comprising the steps of:

(a) contacting one side of a size selective molecularly permeable membrane with a latex solution to be analyzed, the membrane being permeable to low molecular weight components;

(b) contacting the opposite side of the membrane with dialysate fluid;

(c) permeating low molecular weight components in the serum phase of the latex solution through the membrane to the dialysate fluid for a known amount of time;

(d) displacing the dialysate fluid from contact with the membrane after a known amount of elapsed permeation time;

(e) capturing an aliquot sample of the displaced dialysate fluid;

(f) adding the captured sample to a chromatographic column;

(g) adding eluent to the column to elute the sample; and (h) analyzing the sample for serum phase species of interest.

2. The method of claim 1 wherein the size selective molecularly permeable membrane is a hollow fiber.

3. The method of claim 1 wherein the dialysate fluid is water.

4. The method of claim 1 wherein the aliquot of dialysate fluid is captured in a sample injection valve.

5. The method of claim 4 wherein the eluent is $H_2SO_4$.

6. In a liquid chromatography apparatus with a chromatographic column, a sample injection valve, a pump for pumping eluent through the column, and a detector, the improvement which comprises:

(a) a membrane device in communication with the sample injection valve, said device comprising: a reservoir adapted for containing latex solution to be analyzed and a size selective molecularly permeable membrane having one side of the membrane in contact with the latex solution and having the opposite side of the membrane in contact with a dialysate fluid; and (b) means communicating with the membrane device for displacing the dialysate fluid from contact with the membrane directly to the sample injection valve.

7. The apparatus of claim 1 wherein the size selective molecularly permeable membrane is a hollow fiber.

8. The apparatus of claim 1 wherein the dialysate fluid is water.

9. The apparatus of claim 1 wherein the means for displacing the dialysate fluid is a syringe.

* * * * *